(12) United States Patent
Fitzpatrick

(10) Patent No.: US 7,646,899 B2
(45) Date of Patent: Jan. 12, 2010

(54) APPARATUS AND METHODS OF DETERMINING MARKER ORIENTATION IN FIDUCIAL REGISTRATION

(75) Inventor: J. Michael Fitzpatrick, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 762 days.

(21) Appl. No.: 10/543,706

(22) PCT Filed: Feb. 4, 2004

(86) PCT No.: PCT/US2004/003070

§ 371 (c)(1),
(2), (4) Date: Mar. 3, 2006

(87) PCT Pub. No.: WO2004/070655

PCT Pub. Date: Aug. 19, 2004

(65) Prior Publication Data

US 2006/0147100 A1 Jul. 6, 2006

Related U.S. Application Data

(60) Provisional application No. 60/444,699, filed on Feb. 4, 2003.

(51) Int. Cl.
*G06K 9/00* (2006.01)
(52) U.S. Cl. .................. 382/128; 382/131; 382/132
(58) Field of Classification Search .......... 382/128–132
See application file for complete search history.

(56) References Cited

U.S. PATENT DOCUMENTS 5,094,241 A    3/1992   Allen
5,394,457 A    2/1995   Leibinger et al.
5,469,847 A   11/1995   Zinreich et al.
6,419,680 B1   7/2002   Cosman et al.
2001/0010004 A1 7/2001  Traxel et al.

OTHER PUBLICATIONS

Fitzpatrick, J. M. et al., "Registration, Medical Image Processing, vol. II of the Handbook of Medical Imaging," M. Sonka and J. M. Fitzpatrick, ed., SPIE Press (Jul. 2000).
Yan, C. H. et al. "A New Frame-Based Registration Algorithm, Medical Physics," vol. 25 No. 1, pp. 121-128 (Jan. 1998).
Maurer, Jr., C. R. et al., "Registration of Head Volume Images Using Implantable Fiducial Markers," IEEE Transactions on Medical Imaging, vol. 16, pp. 447-462 (Aug. 1997).
Wang, M. Y. et al., "An Automatic Technique For Finding And Localizing Externally Attached Markers In CT and MR Volume Images Of The Head," IEEE Transactions ott Biomedical Engineering, vol. 43, pp. 627-637 (Jun. 1996).
M. Y. Wang, "Fiducial Marker Recognition and Localization for Image-Guided Surgery Using Point-Based Registration," Ph. D. Dissertation, Computer Science, Vanderbilt University, Nashville, TN (May 1998).
Fitzpatrick, J. M., et al., "Predicting Error In Rigid-Body, Point-Based Image Registration," IEEE Transactions on Medical Imaging, vol. 17, pp. 694-702 (Oct. 1998).

*Primary Examiner*—Wesley Tucker
(74) *Attorney, Agent, or Firm*—Morris, Manning & Martin LLP; Tim Tingkang Xia

(57) ABSTRACT

A method for determining an orientation of a base (130) to which a fiducial marker (110) is detachably mounted. The method includes the steps of determining the axis of symmetry for the fiducial marker and choosing the determined axis of symmetry of the fiducial marker (110) as the axis of symmetry of the base (130).

36 Claims, 6 Drawing Sheets

APPARATUS AND METHODS OF DETERMINING MARKER ORIENTATION IN FIDUCIAL REGISTRATION

CROSS-REFERENCE TO RELATED PATENT APPLICATION

This application claims the benefit, pursuant to 35 U.S.C. §119(e), of provisional U.S. Patent Application Ser. No. 60/444,699, filed Feb. 4, 2003 entitled "Apparatus and methods of determining marker orientation in fiducial registration" by J. Michael Fitzpatrick, the disclosure for which is hereby incorporated herein in its entirety by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [1] represents the 1st reference cited in the reference list, namely, J. M. Fitzpatrick, D. L. G. Hill, and C. R. Maurer, Jr., Registration, *Medical Image Processing*, Volume II of the Handbook of Medical Imaging, M. Sonka and J. M. Fitzpatrick, ed., SPIE Press (July, 2000).

FIELD OF THE INVENTION

The present invention generally relates to determination of the orientation of a fiducial marker and image registration, and in particular to the utilization of the orientations of fiducial markers in image guidance and in three-dimensional image registration with two fiducial markers.

BACKGROUND OF THE INVENTION

Recent years have seen the development of diagnostic techniques that allow the practicing clinician to obtain high fidelity views of the anatomical structure of the human body. Imaging systems such as computed tomographic (CT) x-ray imagers, positron emission tomographic (PET) scanners, single photon emission computed tomography (SPECT) scanners and nuclear magnetic resonance imaging (MRI) machines have provided clinicians with the ability to improve visualization of the anatomical structure of the human body without surgery or other invasive techniques. In lieu of exploratory surgery, the patient can be scanned by these imaging systems, and the anatomical structure of the patient can be reproduced in a form for evaluation by a trained doctor.

A problem associated with such scanning techniques concerns the accurate selection and comparison of views of identical areas in images that are obtained at different times or obtained essentially at the same time using different image modalities, e.g., CT, MRI, SPECT, and PET.

This problem has two aspects. First, in order to relate the information in an image of the anatomy to the anatomy itself, it is necessary to establish a one-to-one mapping between points in the image and points of anatomy. This is referred to as registering image space to physical space.

The second aspect concerns the registration of one image space onto another image space. The goal of registering two arbitrarily oriented three-dimensional images is to align the coordinate systems of the two images such that any given point in the scanned anatomy is assigned identical addresses in both images. The calculation of the rigid body transformation necessary to register the two coordinate systems requires knowledge of the coordinate vectors of at least three points in the two systems. Such points are called fiducial points or fiducials, and the fiducials used are the geometric centers of markers, which are called fiducial markers. These fiducials are used to correlate image space to physical space and to correlate one image space to another image space. The fiducial markers provide a constant frame of reference visible in a given imaging mode to make registration possible.

The general technique for using fiducial markers to obtain registration of image data across time includes implanting within a portion of a human body a series of three fiducial markers whose location can be determined in the image space.

Generally speaking, fiducial markers can be either temporary or permanent with respect to the duration of their placement within the human body. Permanent markers are placed entirely beneath the epidermis of the skin for extended periods of time. Temporary markers have two parts: a base that is implanted into bone, and a temporary fiducial marker portion that is attached to the base for brief intervals of time. In the temporary marker, the fiducial marker portion protrudes from the skin.

In both the temporary and the permanent markers, the marker portion may take the form of a hollow container that is charged with aqueous imaging agents to provide imaging capability in the desired imaging modality or modalities.

Whichever type of marker is employed, its precise location, or more accurately, the precise location of the geometric center of the imageable portion of the marker must be determined with respect to a defined external coordinate system in physical space. With respect to permanently implanted markers, ultrasound can be used to determine non-invasively the location of the fully implanted marker. Other techniques can be employed with respect to temporary, externally protruding markers. One method involves in bringing the tip of an external probe whose location in physical space is known into proximity with the marker itself. However, this may result in significant errors in the location of the precise volumetric centroid of the imaging portion of the marker.

Thus, fiducial markers have been successfully employed in image-guided surgical procedures to provide positional information based on pre-operative images. In the standard technique, centroids of three or more markers are localized in both image space and physical space. The localized positions are used in a closed-form algorithm to determine the three-dimensional rigid-body transformation that will register the two spaces in the least-squares sense.

Rigid-body, point-based registration is a standard means for registering two three-dimensional images of a common object when three points are localized in each image. Accurate input points may be obtained by adding fiducial markers to the object and localizing their centroids. Closed-form algorithms for registering point sets have been available since the 1960's and are reviewed in [1]. Unless the markers are spherically symmetric, their orientations, as well as their centroids, can be estimated from their images. Marker orientations can then be used as an adjunct to marker centroids to achieve rigid-body registration.

Therefore, among other things, there always is a need to develop new system and methods that can provide better and more complete information about the marker orientations.

SUMMARY OF THE INVENTION

The present invention, in one aspect, relates to a method for determining the orientation of a base to which a fiducial marker is detachably mounted. The base has an axis of symmetry, $a_b$, representing the orientation of the base, a threaded portion at a first end that is threaded securely into a portion of a human anatomy at a predetermined location, such as the skull or other desired bone tissue of a human body, and an engagement portion at a second end opposing the first end. The fiducial marker is detachably mounted to the engagement portion of the second end of the base. The fiducial marker has an axis of symmetry, $a_m$, which represents the orientation of the fiducial marker. For a cylindrical fiducial marker, the axis of symmetry, $a_m$, is an axis having a cylindrical symmetry.

In one embodiment, the method includes the steps of determining the axis of symmetry for the fiducial marker and choosing the determined axis of symmetry of the fiducial marker as the axis of symmetry of the base.

The determining step includes the steps of acquiring an image having the fiducial marker from the portion of the human anatomy, such as the head of a human, segmenting the fiducial marker into a plurality of voxels from the acquired image, estimating the centroid of the fiducial marker from the segmented fiducial marker image, and estimating the axis of symmetry of the fiducial marker at the estimated centroid. The determining step further includes the steps of simulating an image of the fiducial marker at the estimated centroid and the estimated axis of symmetry, registering the simulated image of the fiducial marker with the acquired image of the fiducial marker so as to obtain a registered centroid and a registered axis of symmetry of the fiducial marker in the acquired image, and updating the estimated centroid and the estimated axis of symmetry of the fiducial marker to the registered centroid and the registered axis of symmetry of the fiducial marker, respectively. Moreover, the determining step includes the step of repeating the simulating step, the registering step and the updating step until both differences between the estimated centroid and the registered centroid and differences between the estimated axis of symmetry and the registered axis of symmetry are substantially small. Additionally, the determining step includes the step of choosing the last registered axis of symmetry as the axis of symmetry of the fiducial marker thereafter.

In one embodiment, the step of estimating the centroid of the fiducial marker can be performed with an intensity weighting method. The step of estimating the axis of symmetry of the fiducial marker includes the steps of decomposing principal axes of the fiducial marker at the estimated centroid of the fiducial marker, calculating moments of inertia for the decomposed principal axes, and identifying the axis of the symmetry from the calculated moment of inertia. For a cylindrical fiducial marker, the moment of inertia of the axis of the symmetry is equal to $d^2/8$, where d is the diameter of the cylindrical fiducial marker.

The step of simulating the image of the fiducial marker includes the steps of setting intensity of a voxel that is completely inside the fiducial marker to the maximum intensity values, $I_{max}$, of the voxel values in the acquired image, setting intensity of a voxel that is completely outside the fiducial marker to zero, and defining intensity of a voxel that crosses the edge of the fiducial marker as a form of $I=(V_{in}/V)I_{max}$, where $V_{in}$ is the volume of the voxel that lies inside the fiducial marker, V is the volume of the entire voxel, and $I_{max}$ is the voxel intensity of the voxel completely inside the fiducial marker. In one embodiment, $V_{in}/V$ is calculated in the following steps: dividing the voxel that crosses the edge of the fiducial marker into m×n×p subvoxels, where each of m, n, p is an integer, designating a subvoxel as being inside the fiducial marker if its centroid is inside the fiducial marker and as being outside the fiducial marker if its centroid is outside the fiducial marker, accumulating the number of the subvoxels whose centroids are inside the fiducial marker, and determining $V_{in}/V$ by dividing the accumulated number by the total number, m×n×p, of the subvoxels of the voxel.

The step of registering the simulated image of the fiducial marker with the acquired image of the fiducial marker can be performed with an optical flow registration.

In one embodiment of the present invention, the acquired image is a tomographic image, which is at least one of a computed tomographic (CT) image and a magnetic resonance (MR) image.

In another aspect, the present invention relates to a system of image guidance through a portion of a human anatomy. In one embodiment, the system has a number, M, of bases. Each base has an axis of symmetry, $a_b$, which represents the orientation of the base, a threaded portion at a first end that is threaded into the portion of a human anatomy at a predetermined location, such as the head of a human, and an engagement portion at a second end opposing the first end. The system further has a number M of fiducial markers. Each fiducial marker has an axis of symmetry, $a_m$, and is detachably mounted to a corresponding base at the engagement portion of the second end of the base. In one embodiment, the axis of symmetry of the base and the axis of symmetry of the fiducial marker are identical when the fiducial marker is detachably mounted to the base, that is, $a_b=a_m$. Furthermore, the system has a platform for image guidance. The platform has a number M of bosses, which each boss is mounted to the engagement portion of a corresponding base such that the boss lines up with the base.

Moreover, the system has means for acquiring a three-dimensional tomographic image from the portion of the human anatomy containing the number M of fiducial markers. The three-dimensional tomographic image includes at least one of a computed tomographic (CT) image and a magnetic resonance (MR) image, and is adapted for identifying the centroid and the axis of symmetry of each fiducial marker so as to determine the position and orientation of its corresponding base. The acquiring means can be a CT x-ray imager, a PET scanner, a SPECT scanner, or an MRI machine. The system further has means for identifying the centroid and axis of symmetry of a fiducial marker from the three-dimensional tomographic image.

In one embodiment, the number M is an integer greater than one (1). Each of the bases is a solid cylinder. Each of the fiducial markers has a cylindrical cavity, where the cylindrical cavity is filled with an imagable material. The imagable material includes a fluid that is visible in a computed tomographic (CT) image and a magnetic resonance (MR) image.

In yet another aspect, the present invention relates to a method for registering a first image with a second image. The first image has at least two fiducial markers each having an axis of symmetry. The second image has at least two fiducial markers each having an axis of symmetry and corresponding to a fiducial marker in the first image. The at least two fiducial markers of the first image and the at least two fiducial markers of the second image are orientated such that the axis of symmetry of at least one of the at least two fiducial markers for each of the first image and the second image is nonparallel to a line on which the at least two fiducial markers lie in the corresponding image. In one embodiment, the fiducial marker is a cylinder, where the axis of symmetry of the fiducial marker is an axis having a cylindrical symmetry The method, according to one embodiment of the present invention, includes the steps of finding the centroid of each of the at least two fiducial markers in the first image, finding the axis of the symmetry of each of the at least two fiducial markers in the first image, and constructing a set of points for the at least two fiducial markers in the first image, where the set of points includes a vector of the centroid and an unit vectors of the axis of the symmetry of each of the at least two fiducial markers in the first image. Furthermore, the method includes the step of repeating the step of finding the centroid of each of the at least two fiducial markers, the step of finding the axis of the symmetry of each of the at least two fiducial markers in the second image and the step of constructing a set of points for the at least two fiducial markers in the second image. The set of points in the second image corresponds to the set of points in the second image. Moreover, the method includes the step of determining a transformation matrix from the set of points in the first image and the set of points in the second image so as to register the first image with the second image.

In one embodiment, the transformation matrix corresponds to a rigid-body transformation, and is calculated with a closed-form algorithm. The closed-form algorithm includes a singular value decomposition (SVD) method.

In a further aspect, the present invention relates to a system for registering a first image with a second image. The first image has at least two fiducial markers each having an axis of symmetry. The second image has at least two fiducial markers each having an axis of symmetry and corresponding to a fiducial marker in the first image. The at least two fiducial markers of the first image and the at least two fiducial markers of the second image are orientated such that the axis of symmetry of at least one of the at least two fiducial markers for each of the first image and the second image is nonparallel to a line on which the at least two fiducial markers lie in the corresponding image. In one embodiment, the fiducial marker is a cylinder, where the axis of symmetry of the fiducial marker is an axis having a cylindrical symmetry.

In one embodiment, the system has a central processing unit (CPU) which is programmed for performing the steps of finding the centroid of each of the at least two fiducial markers in the first image, finding the axis of the symmetry of each of the at least two fiducial markers in the first image, and constructing a set of points for the at least two fiducial markers in the first image, where the set of points includes a vector of the centroid and an unit vectors of the axis of the symmetry of each of the at least two fiducial markers in the first image. The central processing unit (CPU is further programmed for performing the steps of repeating the step of finding the centroid of each of the at least two fiducial markers, the step of finding the axis of the symmetry of each of the at least two fiducial markers in the second image and the step of constructing a set of points for the at least two fiducial markers in the second image. The set of points in the second image corresponds to the set of points in the second image. Moreover, the central processing unit (CPU) is programmed for performing the steps the step of determining a transformation matrix from the set of points in the first image and the set of points in the second image so as to register the first image with the second image. In one embodiment, the central processing unit (CPU) is associated with a computer. The computer itself can be a PC, a workstation, or a part of a network.

In one embodiment, the transformation matrix corresponds to a rigid-body transformation, and is calculated with a closed-form algorithm. The closed-form algorithm includes a singular value decomposition (SVD) method.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

FIG. 4 illustrates a marker configuration in the x-y plane for image registration according to one embodiment of the present invention. Two fiducial markers with nominal angular orientations are located at [x,y,z]=[−50,0,0] and [+50,0,0], respectively. The Xs show positions of a third marker. The black circle is a target point, located at [x,y,z]=[0,+50,0], to be registered with.

DETAILED DESCRIPTION OF THE INVENTION

Figure 1B:
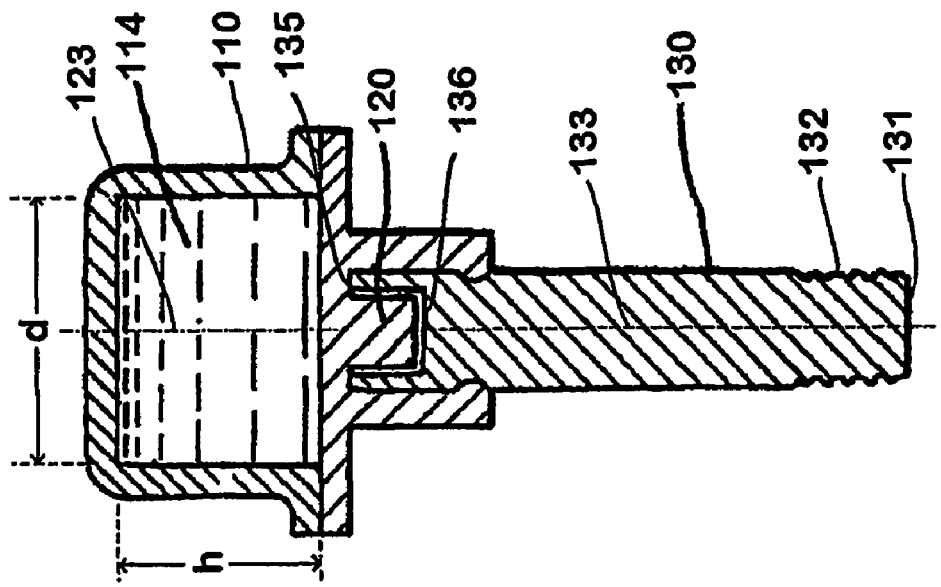
FIG. 1B is a cross-sectional view of the fiducial marker mounted to the base shown in FIG. 1A as viewed along line 1B-1B.

Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

Definitions

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "centroid" refers to a point that represents the mean position of a fiducial marker.

As used herein, "base" refers to a post to which a fiducial marker is mounted.

As used herein, "axis of symmetry" refers to an axis that uniquely represents the orientation of a fiducial marker, or a base to which a fiducial marker is mounted, depending upon the specific context where the term is used.

Overview of the Invention

Figure 1A:
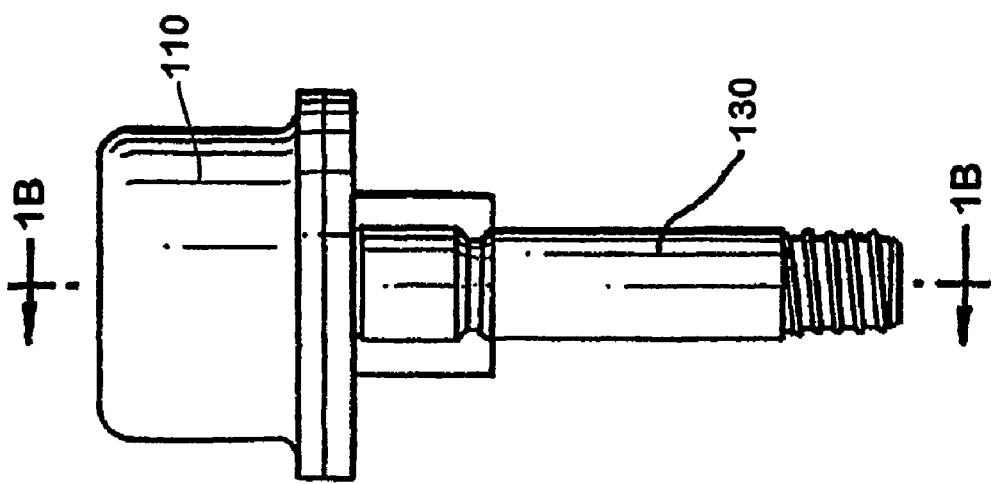
FIG. 1A is an elevational view of a fiducial marker mounted to a base according to one embodiment of the present invention.

In one aspect, the present invention relates to a method for determining an orientation of a base to which a fiducial marker is detachably mounted. In one embodiment, as shown in FIGS. 1A and 1B, the base 130 has an axis of symmetry 133, which uniquely represents the orientation, $a_b$, of the base 130. The base 130 also has a threaded portion 132 at a first end 131 that enables a professional such as a surgeon to securely mount the base 130 to a portion of a human anatomy at a predetermined location, such as the skull or other desired bone tissue of a human body, and an engagement portion 136 at a second end 135 opposing the first end 131, which is adapted for securely and detachably engaging with a fiducial marker 110 with the base 130. The fiducial marker 110 is detachably mounted to the second end 135 of the base 130, through its protruding boss 120 engaged with the engagement portion 136 of the base 130. The fiducial marker 110 has an axis of symmetry 123, which uniquely represents the orientation, $a_m$, of the fiducial marker 110. For a cylindrical fiducial marker 110, the axis of symmetry 123 is an axis having a cylindrical symmetry. The fiducial marker 110 further has a cavity 114, where the cavity 114 is filled with an imagable material such as a fluid that is visible in a computed tomographic (CT) image and/or a magnetic resonance (MR) image.

In one embodiment, the method for determining the orientation of a base includes the steps of determining the axis of symmetry for the fiducial marker and choosing the determined axis of symmetry of the fiducial marker as the axis of symmetry of the base.

Figure 2:
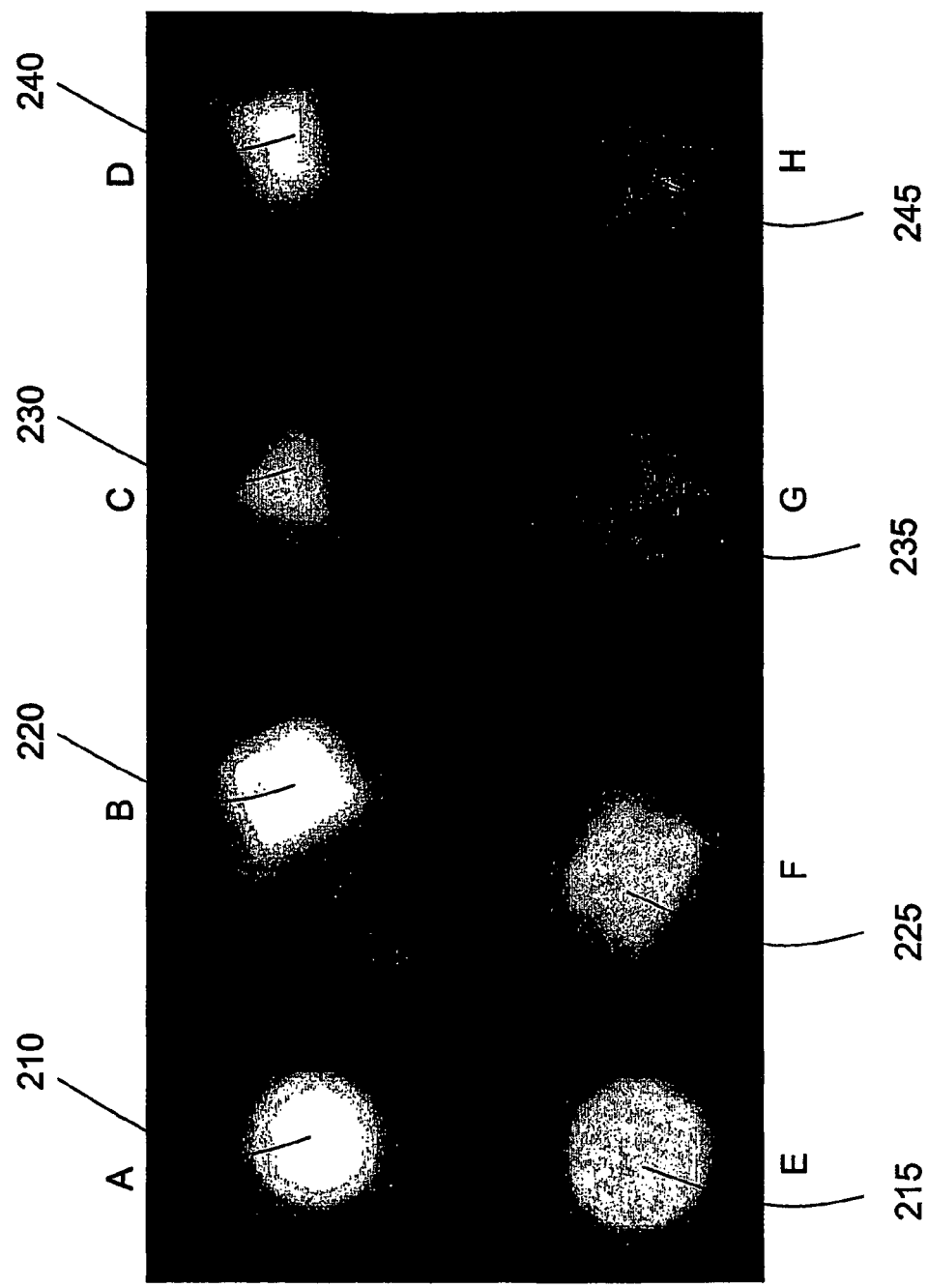
FIG. 2 shows computed tomographic (CT) images and magnetic resonance (MR) images of fiducial markers, respectively: (A)-(D) are CT images and (E)-(H) are MR images.

In the determining step, at first, an image containing the fiducial marker is acquired from the portion of the human anatomy, such as the head of a human. The image can be either a CT image or MR image. As shown in FIG. 2, images 210, 220, 230 and 240 are CT images of a fiducial marker at various orientations, while images 215, 225, 235 and 245 are MR images of the fiducial marker at the corresponding orientations, respectively. Comparing with CT images 210, 220, 230 and 240, MR images 215, 225, 235 and 245 are relative dim in this situation. Secondly, the fiducial marker is segmented into a plurality of voxels from the acquired image. Thirdly, the centroid of the fiducial marker is estimated from the segmented fiducial marker image. Then the axis of symmetry of the fiducial marker is estimated at the estimated centroid. At the estimated centroid and axis of symmetry, an image of the fiducial marker is simulated. The simulated image of the fiducial marker then is registered with the acquired image of the fiducial marker so as to obtain a registered centroid and a registered axis of symmetry of the fiducial marker in the acquired image. The estimated centroid and axis of symmetry of the fiducial marker are updated to the registered centroid and axis of symmetry of the fiducial marker, respectively. The simulating step, the registering step and the updating step are repeated until both differences between the estimated centroid and the registered centroid and differences between the estimated axis of symmetry and the registered axis of symmetry are substantially small. Now, the last registered axis of symmetry is substantially identical to anf therefore chosen as the axis of symmetry of the fiducial marker. Detailed descriptions of practices of these steps are further given in the following section in the specification.

In another aspect, the present invention relates to a system of image guidance through a portion of a human anatomy. Such a system, among other things, can be utilized by a professional such a neurosurgeon to navigate through the anatomical structure of the human body. Referring to FIGS. 3A-3D, in one embodiment, the portion of the human anatomy includes the head of a human 342, the system 300 has a number, M, of bases 330, M being an integer greater than one, although only one base 330 is shown therein. Each base 330 has an axis of symmetry 333 that represents the orientation, $a_b$, of the base 330, a threaded portion 332 at a first end 331 that enables a professional such as a neurosurgeon to securely mount the base 330 into the portion of a human anatomy, such as the head of a human 342, at a predetermined location. In the illustrated example of FIGS. 3C and 3D, M=3, and the predetermined locations of the base 330 are at 340a, 340b and 340c, respectively. Each base 330 has an engagement portion 336 at a second end 335 opposing the first end 331. The system 300 further has a number M of fiducial markers 310. Each fiducial marker 310 has an axis of symmetry 323, $a_m$, and is detachably mounted to a corresponding base 330 at the engagement portion 336 of the second end 335 of the base 330. In one embodiment, the axis of symmetry 333 of the base 330 and the axis of symmetry 323 of the fiducial marker 310 are coincident when the fiducial marker 310 is mounted to the base 330, that is, $a_b = a_m$. The bases 330 and fiducial markers 310 are parts of the Acustar system, which is manufactured by Z-Kat, Inc., Hollywood, Fla. In one embodiment of the present invention, each of the bases 330 is a solid cylinder having a height of 14 mm and a diameter of 3 mm with threads 332 at the first end 331 for screwing into holes in bone. Each of the markers 310 is a hollow cylinder having approximately a height of 5 mm and a diameter of 7 mm, filled with a fluid that is visible in both CT and MR images.

In using of the system 300, a three-dimensional tomographic image including the number M of fiducial markers 310 mounted to the respective bases 330 is acquired from the portion of the human anatomy, such as the head of the human 342, where the bases 330 attached to. The three-dimensional tomographic image includes a computed tomographic (CT) image and/or a magnetic resonance (MR) image, and is adapted for identifying the centroid and the axis of symmetry 323 of a fiducial marker 310 mounted to a corresponding base 330, and therefore determining the position and orientation of the base 330.

Figure 3B:
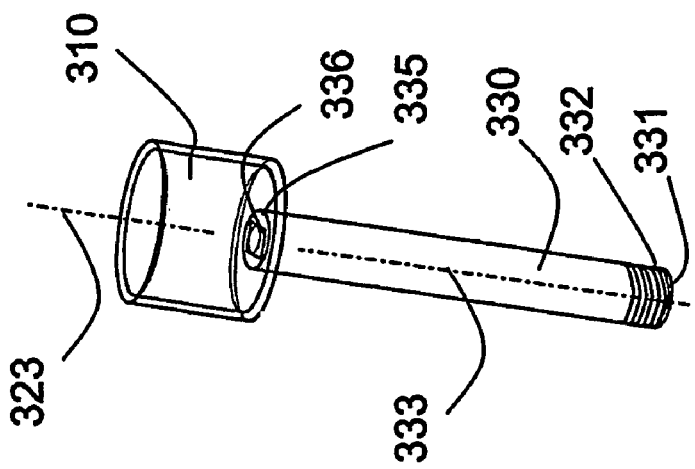
FIG. 3B shows systematically a fiducial marker mounted to bases according to one embodiment of the present invention.
Figure 3A:
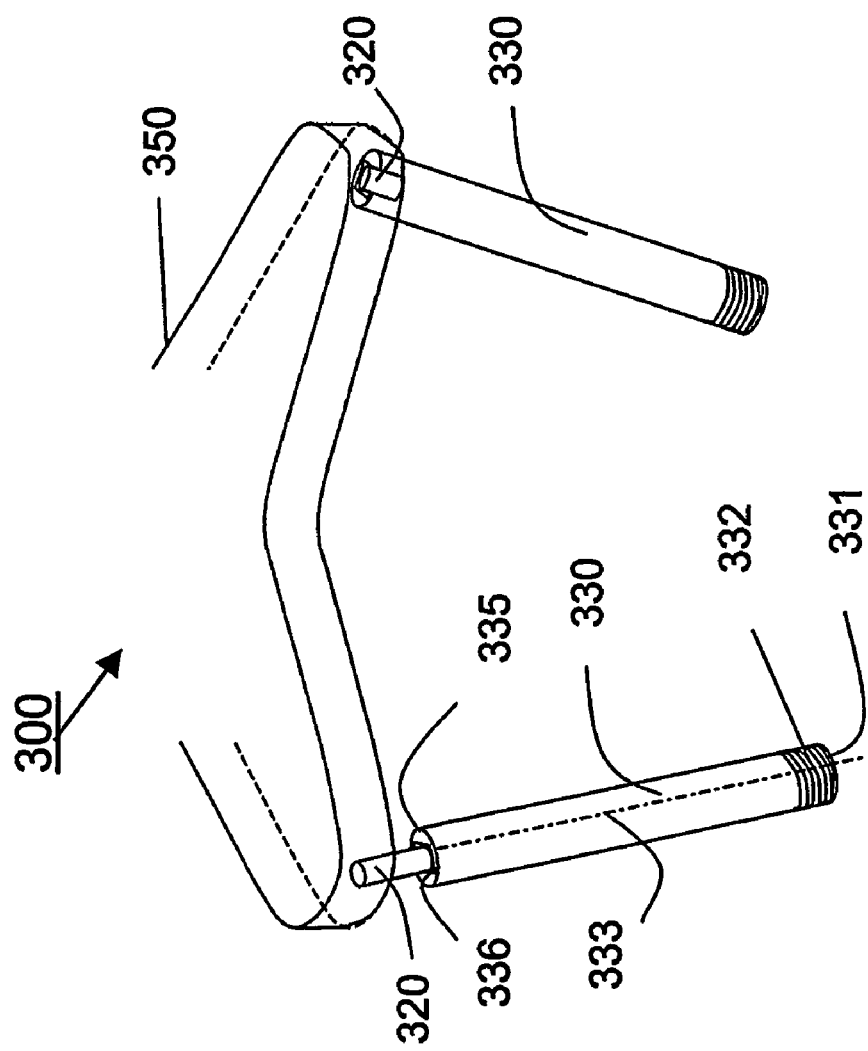
FIG. 3A shows systematically a platform attached to bases according to one embodiment of the present invention.
Figure 3D:
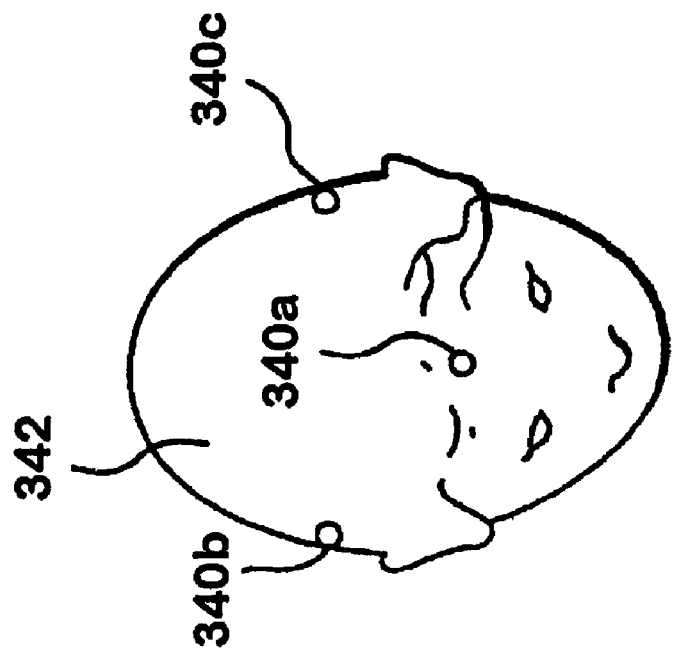
FIG. 3D is a front view of the illustrated example shown in FIG. 3C.
Figure 3C:
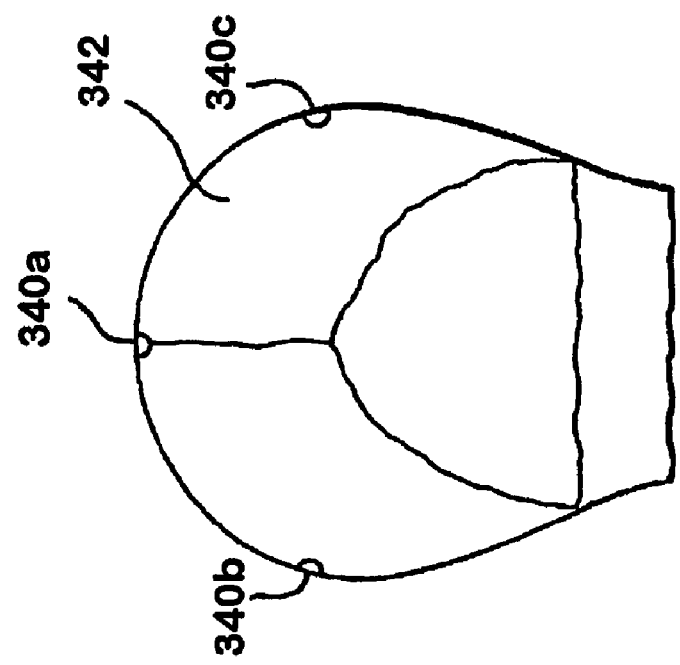
FIG. 3C is a back view of an illustrated example of localizations of bases in a head portion of a human anatomy according to one embodiment of the present invention.

Furthermore, the system 300 has a platform 350. The platform 350 has a number M of bosses 320 with each mounted to a corresponding base 330 at the engagement portion 336 of the second end 335 of the base 330. The attachment of the platform 350 to the bases 330 requires that both the position of the second end (tip) 335 and the orientation of each base 330 be determined. The platform 350 is customized for a human anatomy so that it fits the bases 330 in the positions that the bases 330 are attached to the head of the human anatomy. As shown in FIG. 3A, the orientations of the bases 330 are arbitrary. This arbitrariness arises because the orientations depend on the shape of the head of the human anatomy and the locations of the bases 330 on the head as chosen by a professional such as a surgeon. The platform 350 is designed and manufactured, based on the position and the orientation of each base 330, such that when a boss 320 is mounted to its corresponding base 330 the boss 320 lines up with the base 330. The position of the second end (tip) 335 and the orientation of a base 330 are determined through calculating the centroid and orientation of a corresponding fiducial marker 310 which is mounted to the base 330. According to one embodiment to the present invention, the orientation of a base 330 is same as that of a marker 310 mounted to the base 330, and the position of the second end (tip) of the base 330 is a point that is 3 mm down from the centroid of the marker 310 on the axis of symmetry 323 of the marker 310. The centroid and orientation of the marker 310 are determined from the acquired three-dimensional tomographic image containing the marker. In one embodiment, the platform 350 is manufactured by Fred Herr Corporation (Bowdoinham, Me.). The alignment accuracy requirement is estimated by employees at Fred Herr Corporation to be on the order of 5 degrees.

Figure 4:
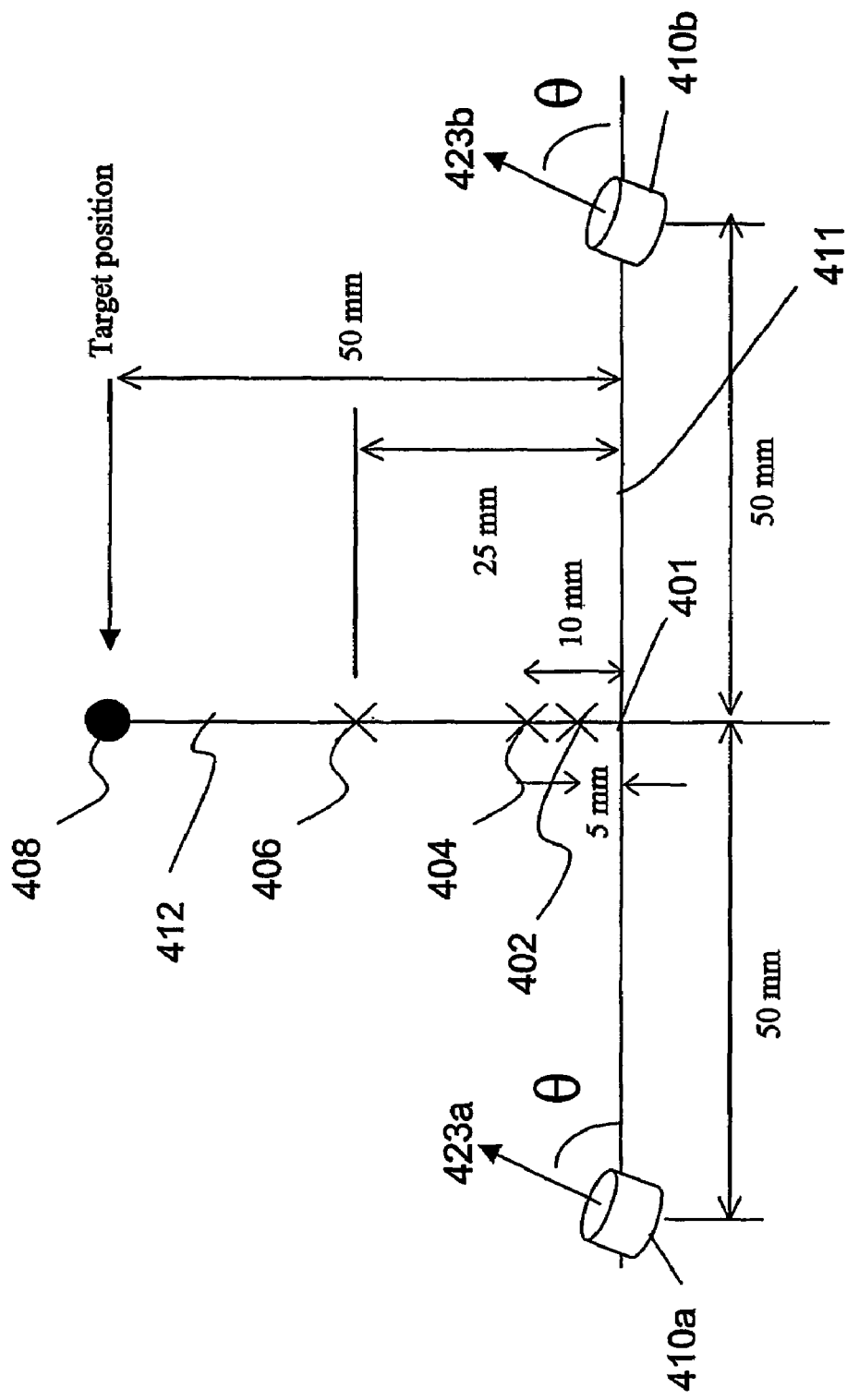

In yet another aspect, the present invention relates to a method for registering a first image with a second image. Referring to FIG. 4, where a systematical configuration of the fiducial markers for the image registration is shown. The first image has at least two fiducial markers each having an axis of symmetry. The at least two fiducial markers can be markers 410a and 410b and its corresponding axis of symmetry are represented 423a and 423b, respectively, in FIG. 4. The second image has at least two fiducial markers and each having an axis of symmetry and corresponding to a fiducial marker in the first image. The at least two fiducial markers 410a and 410b in the first image and the at least two fiducial markers in the second image are orientated such that the axis of symmetry of at least one of the at least two fiducial markers is nonparallel to a line 411 on which the at least two fiducial markers lie in the corresponding image.

In one embodiment, the method includes the following steps: (1) finding the centroid of each of the at least two fiducial markers 410a and 410b in the first image, (2) finding the axis of the symmetry of each of the at least two fiducial markers 410a and 410b in the first image, (3) constructing a set of points for the at least two fiducial markers 410a and 410b in the first image, where the set of points includes a vector of the centroid and an unit vectors of the axis of the symmetry of each of the at least two fiducial markers 410a and 410b in the first image. (4) repeating steps (1)-(3) in the second image for the at least two fiducial markers in the second image so as to construct a set of points for the at least two fiducial markers in the second image corresponding to the set of points in the first image, and (5) determining a transformation matrix from the set of points in the first image and the set of points in the second image so as to register the first image with the second image.

Methods

Referring back to FIGS. 1 and 2, the marker 110, shown in FIGS. 1A and 1B, is designed for use in an image-guided surgery [1]. In one embodiment, the fiducial marker is a hollow-plastic, sealed container whose inner volume 114 is in the shape of a cylinder having height $h=5$ mm and diameter $d=7$ mm. The inner volume 114 is filled with a fluid that is imagable in both CT and MR [3]. (The dimensions indicated on here and the remainder of the specification are illustrative only, and reflect only one possible embodiment.) The CT images of the marker 110 are shown in FIGS. 2A-2D, where images 210, 220, 230 and 240 are respectively the image of the marker 110 for different marker orientations, while the MR images for the corresponding orientations are shown in FIGS. 2E-2H, indicated by 215, 225, 235 and 245, respectively.

Determinations of Centroid and Orientation of a Marker

The centroid and orientation of a fiducial marker are determined by iteratedly registering a simulated image (model) of the fiducial marker with an acquired image of the fiducial marker until incremental motions between the simulated maker and that in the acquired images are substantially small. To simulate the image of the fiducial marker, a starting point of the centroid and orientation of the fiducial marker needs being provided. This can be obtained by making an initial estimate of the orientation of the fiducial marker from the acquired image, which includes applying an intensity weighting method [4] to find the centroid of the fiducial marker in the acquired image, decomposing principal axes of the fiducial marker at the centroid, calculating moments of inertia for the decomposed principal axes, and identifying the axis of the symmetry from the calculated moment of inertia. The latter step takes advantage of the fact that the moment of inertia of the fiducial marker about its axis of symmetry is significantly different from the moments about its other two principal axes. The axis of the symmetry of the fiducial marker is referred to the orientation of the fiducial marker. To refine the initial estimate, the simulated image (model) is registered with the acquired image of the fiducial marker using optical flow [5].

Optical flow determines an incremental local motion at each point in one image, in this case the simulated image (model), that will reduce the intensity difference at that point relative to a second image, in this case the acquired image. It requires a good starting point, which is provided by initializing the simulated image (model) at the centroid (position) and orientation determined in the previous steps. Because the optical flow is underdetermined [5], it also requires a constraint on the motion, which is easily provided here by imposing rigidity. With rigidity, the solution is over determined, so a rigid motion is chosen that minimizes the total squared difference in intensity over the entire marker. The resulting incremental motion is applied to the simulated image (model), and the process is repeated until the motion is small. The final direction of the axis of symmetry of the simulated model is the orientation of the fiducial marker.

Suppose an initial estimate of the centroid and orientation of the fiducial marker are obtained. To refine the result, the displacement, or the movement between the initial estimate and the fiducial marker in the acquired image needs being found. Then the fiducial marker is moved from the initial guess by the estimated motion. The object motion can be estimated from image intensity changes in sequential images with the optical flow method [5]. The optical flow is based on the assumption that the intensity of the object does not change during the motion. After an initial guess of the centroid (position) and orientation of the fiducial marker is obatined, a simulated marker at this position and orientation is generated based on a known shape of the fiducial marker. Then the simulated marker is compared with the real fiducial marker in the acquired image. If the two images are different, the motion between the two images is calculated using the optical flow method. The centroid (position) and orientation of the fiducial marker are then updated. These steps are iterated until the motion is sufficiently small.

Initial Estimates

After the fiducial marker is segmented into a plurality of voxels from the acquired image, for example, one of images in FIG. 2, the centroid of the fiducial marker can be estimated with an intensity weighting method [4], which is the form of:

$$c = \Sigma_i (I_i - I_0) v_i / \Sigma_i (I_i - I_0) \tag{1}$$

where $I_i$ is the intensity of the ith voxel centered at $v_i = (v_x, v_y, v_z)$, and $I_0$ is the intensity of an empty voxel.

The orientation of the fiducial marker is estimated by decomposing its principal axes. In one embodiment of the present invention, the fiducial marker is a cylinder, which one of the three principal axes of the cylinder has a cylindrical symmetry, which is identified as the axis of symmetry of the fiducial marker by an unit vector a, the other two axes are perpendicular to the principal axis and to each other. For the cylindrical marker, the second moment about the axis of symmetry is $d^2/8$, and the moments about the other two axes are each equal to $h^2/12 + d^2/16$, where d is the diameter, and h is the height of the cylindrical marker. In one example, the marker height h=5 mm and the marker diameter d=7 mm, consequently, the moment about the axis of symmetry is equal to 6.125 mm$^2$, which is 19% larger than that of the other two axes, which are equal to 5.146 mm$^2$. Thus, the axis with the largest second moment is identified as the estimated axis of symmetry. Experiments show that such a selection nearly always selects correctly among the three axes.

In another embodiment of the present invention, the axis of symmetry of a fiducial marker is determined as follows: generating a simulated marker located on the estimated centroid for each possible orientation and then comparing differences between the simulated marker for each possible orientation and the real marker. The axis of symmetry of which the simulated marker is the most similar to the real marker is identified as the orientation of the fiducial marker.

Marker Simulation

After the initial estimates of the centroid (position) and orientation of the fiducial marker are obtained, a marker image is simulated at that position and orientation and compared to the acquired image of the fiducial marker. By adjusting the position and orientation to find the best fit of the simulated image to the acquired image of the fiducial marker, both position and orientation of the fiducial marker are refined. In one embodiment of the present invention, the fiducial marker is simulated as follows: each voxel that is completely inside the marker is set as the maximum intensity value of marker voxel values in the acquired image, each voxel completely outside the marker is set to zero, and each voxel near the edge of the marker is set to an intermediate intensity I, where $$I = \frac{V_{in}}{V} I_{max} \tag{2}$$

where $v_{in}$ is the volume of the voxel that lies intersects the marker, v is the volume of the entire voxel, and $I_{max}$ the voxel intensity of the voxel completely inside the marker.

Because of the complex shape of the intersection of cylinder and voxel, it is difficult to calculate the exact volume $v_{in}$ of the intersection. An approximation with a simpler numerical technique is adapted for calculating $V_{in}/V$. In one embodiment, the voxel that crosses the edge of the fiducial marker is divided into m×n×p subvoxels, where m, n, p are an integer, then designating a subvoxel as being inside the fiducial marker if its centroid is inside the fiducial marker and as being outside the fiducial marker if its centroid is outside the fiducial marker, accumulating the number of the subvoxels whose centroids are inside the fiducial marker, and determining $V_{in}/V$ in Eq. (2) by dividing the accumulated number by the total number, mnp, of the subvoxels of the voxel. The computation time of this method is proportional to the number of subvoxels. For example, if m=n=p, *the computation time is of order O(n$^3$). In one embodiment, m=n=p=5 produces an acceptable compromise between efficiency and accuracy. Alternatively, m, n and p may be selected so as to make the side of subvoxel equal to a fixed length, for example, 0.25 mm.

Optical Flow Registration

The method of the optical flow registration comprises a rigid-body three dimensional (3D) image registration. Given an initial guess of a marker position and orientation, the simulated image is registered with the real marker using optical flow, method. The marker position and orientation can be estimated with subvoxel accuracy. The approach is based on the 3D version of the optical flow equation. Let f(x,y,z,t) represent the image intensity at pixel position (x,y,z) and time t, the 3D optical flow constraint equation is:

$$f_t + f_x x_t + f_y y_t + f_z z_t = f_t + \nabla f \cdot u = 0 \tag{3}$$

where $u=(x_t, y_t, z_t)$ is the velocity, or the transformation between f(x,y,z,t) and f(x,y,z,t+Δt) As only the rigid-body motion is considered, the motion can be decomposed into a translation and a rotation. When the rotation angles are small, the motion can be approximately rewritten as:

$$u = Rr + t \approx \theta \times r + t \tag{4}$$

where $t=(t_x, t_y, t_z)$ is the translation vector, $\theta=(\theta_x, \theta_y, \theta_z)$ is the vector of rotation angles around x, y and z axis, respectively, and $r=(r_x, r_y, r_z)=x-x_0$ is the image position relative an origin $x_0$ lying on the axis of rotation. For the ith voxel $(x_i, y_i, z_i)$, Eq. (3) combined with Eq. (4) can be rewritten numerically as:

$$f_{x_i} t_x + f_{y_i} t_y + f_{z_i} t_z + (f_{z_i} r_{y_i} - \rho_i r_z i) \theta_x + (f_{x_i} r_{z_i} - f_{x_i} r_{x_i}) \theta_y + (f_{y_i} r_{y_i} - f_{y_i} r_{x_i}) \theta_z = -\Delta f_i \tag{5}$$

For all the N voxels, Eq. (5) can be written in the matrix form of:

$$Ax=b \quad (6)$$

where A is a N by 6 matrix, $x=(t_x,t_y,t_z,\theta_x,\theta_y,\theta_z)$ is the column vector of the rigid-body motion parameters, and b is a N by 1 column vector. The ith row of A is:

$$[f_{x_i}, f_{y_i}, f_{z_i}, f_{z_i}r_{y_i}-f_{y_i}r_{z_i}, f_{x_i}r_{z_i}-f_{z_i}r_{x_i}, f_{y_i}r_{x_i}-f_{x_i}r_{y_i}] \quad (7)$$

and the ith element of b is the difference between the intensity of the real marker and the simulated marker at the ith voxel.

To solve equation (6), in one embodiment of the present invention, a singular value decomposition (SVD) is employed to get the optimal x in the least square sense. After the transformation is estimated, the centroid (position) and axis of symmetry (orientation) of the marker are respectively updated as follows:

$$c_{new}=Rc_{old}+t,$$

$$\hat{a}_{new}=R\hat{a}_{old}. \quad (8)$$

The above steps are executed iteratively until the registration parameters, such as the differences between $c_{new}$ and $c_{old}$ and the differences between $a_{new}$ and $a_{old}$, are substantially small.

Incorporating Marker Orientation into Registration

Standard point-based, rigid-body image registration determines a rotation matrix and translation vector that provide a transformation that minimizes the sum of squares of the distances between corresponding points in two image spaces. The key step of the standard method of the image registration is to determine the transformation from one image space into the other image space based on two sets of points with each including positions (centroids) of the fiducial markers in the corresponding image space. In one embodiment of the present invention, the two image spaces correspond to a first image and a second image. For each image, there is, in addition to the set of points derived from centroids of the fiducial markers in the image, a set of orientations represented by the axis of symmetry of each marker in the image for use of the image registration. To incorporate this information of the marker orientations into the determination of the transformation, the standard method is extended to accommodate both the set of point of the centroids and the set of the corresponding orientations into one set of points by treating the corresponding orientation as an additional point for the purposes of calculating the rotation. Thus, for $N_p$ points and $N_a$ axes of symmetry there are two sets of the extended points with each having $(N_p+N_a)$ vectors, which are respectively in the forms of:

$$p_i, \ldots, p_{N_p}, \hat{a}_i, \ldots, \hat{a}_{N_a}$$

$$q_i, \ldots, q_{N_p}, \hat{b}_i, \ldots, \hat{b}_{N_a} \quad (9)$$

where $p_i$ and $\hat{a}_i$ represent the point of the centroid and the orientation of the ith fiducial marker in the first image, respectively, which constructs a set of the extended points in the first image, and $q_i$ and $\hat{b}_i$ represent the point of the centroid and the orientation of the ith fiducial marker in the second image, respectively, which constructs a set of the extended points in the second image. The transformation then has the form:

$$p'_i=Rp_i+t,$$

$$a'_i=Ra_i \quad (10)$$

where R is the rotation matrix and t the translation vector for $i=1, \ldots, N_p$.

The standard method of the image registration requires at least three noncollinear points (fiducial markers) be presented in each image. The extended method allows collinear point sets and as few as two points as long as at least one of the axes of symmetry of the two fiducial markers in each image is nonparallel to the line on which the points in that image lie. A systematical configuration of the image registration with two markers, according to one embodiment of the present invention, is illustrated in FIG. 4, where two fiducial markers 410a and 410b are configured 100 mm apart along the x-axis 411, each with a varying value of the angle θ between the axis of symmetry 423a (423b) and the x-axis 411. Accordingly, for the configuration, $N_p=2$ and $N_a=2$ in Eq. (9).

There are several closed-form solutions for determining the transformation [1]. In one embodiment of the present invention, a singular value decomposition (SVD) method [1] is adapted for determining the transformation. As in the standard method the translation vector t is given by the displacement between the weighted means of the two sets of points:

$$t=\bar{q}-\bar{p}, \quad (11)$$

where $$\bar{p}=\Sigma w_i^{(p)}p_i/\Sigma w_i^{(p)}, \quad \bar{q}=\Sigma w_i^{(p)}q_i/\Sigma w_i^{(p)}. \quad (12)$$

Then, a cross-covariance matrix is formed as, $$H = \sum_{i=1}^{N_p} w_i^{(p)} \tilde{p}_i \tilde{q}_i^t + \sum_{i=1}^{N_a} w_i^{(a)} \hat{a}_i \hat{b}_i^t \quad (13)$$

where $$\tilde{p}_i=p_i-\bar{p}_i, \quad \tilde{q}_i=q_i-\bar{q}_i. \quad (14)$$

are displacements of the centroid of the ith fiducial marker from the weighted mean of the sets of points in the first image and the second image, respectively. Superscript t represents a transpose of a vector. The $w_i^{(p)}$ and $w_i^{(a)}$ are weights which may be adjusted according to the certainty of the measurements. In examples set forth below, the weights are all set to 1. The singular value decomposition (SVD) of H is in the form of $UΛV^t=H$, where $U^tU=V^tV=I$, and $V=diag(\lambda_1,\lambda_2,\lambda_3)$ with $\lambda_1 >= \lambda_2 >= \lambda_3 >= 0$, where diag is a diagonal matrix with the indicated elements on the diagonal.

The rotation matrix R is then obtained as, $$R=U^t diag(1,1,det(UV))V, \quad (15)$$

where det(UV) means the determinant of UV.

It should be noticed that the association of a given axis with a given marker has no effect on the resulting transformation. Thus, the interchange of orientations of, for example, markers A and B, while their centroids remain the same, affects neither R nor t. In fact, the positions of the axes (as opposed to their orientations) have no effect on the transformation.

Results of Examples and Implications

Examples according to the present invention are further presented herein both for the determination of the orientation of a single fiducial marker and for image registration based on both points and orientation axes. In the former case, both computer simulations and phantom imaging were employed, while only computer simulations were employed in the latter case. The accuracy of the corresponding method was measured. All computer programs were written using Matlab, Version 6 (The Mathworks, Inc., Natick, Mass.)

Orientation Accuracy

Results from a computer simulation and from phantom imaging are presented. In each case, an orientation of a fiducial marker was represented by a single axis of symmetry. The axis of symmetry was determined using the method described above in the section of "DETERMINATIONS OF CENTROID AND ORIENTATION OF A MARKER". Convergence was achieved in 20 iterations. To determine the accuracy of the method, the measured axis of symmetry $\hat{a}_M$ was compared with the true axis of symmetry $\hat{a}_T$. The error was expressed in terms of the angle between the two axes, $\hat{a}_M$ and $\hat{a}_T$. Because the measured axis was determined from an acquired image of the fiducial marker, this error was called as the *Fiducial Angular Error* (FAE). Accordingly, FAE is expressed as in the form of $FAB=\cos^{-1}(\hat{a}_M \cdot \hat{a}_T)$. In keeping with the standard statistics for fiducial measurement errors, the root-mean-square (RMS) value of FAE was calculated. In all experiments, 20 iterations were sufficient to reach the convergence.

In a first example, marker images were simulated according to the method of the present invention, as described in the section of "DETERMINATIONS OF CENTROID AND ORIENTATION OF A MARKER", to which noises were added. In the example, the marker had a diameter of 7 mm and a height of 5 mm. (The dimensions indicated in the specification are illustrative only, and reflect only one possible embodiment.) A simulated marker image was generated at a given marker centroid (position) and orientation using a value of 255 for the maximum intensity value of voxels, $I_{max}$. Then, zero-mean Gaussian noises were added to the simulated image. Several levels of noises were employed. The method described in the section of "DETERMINATIONS OF CENTROID AND ORIENTATION OF A MARKER" was applied 100 times on the same image with independent noise patterns to determine the RMS value for FAE. Table 1 lists representative results.

TABLE 1

RMS FAE for the simulated marker. Pixel size is 1 × 1 × 2. Orientation is [1, 0, 0].

| | Noise Standard Derivation | | |
|---|---|---|---|
| | 4 | 6 | 8 |
| RMS FAE (degree) | 0.927764 | 1.91489 | 2.311613 |

In a second example, the method was applied to fiducial markers attached to a multi-tiered plastic phantom with each fiducial marker mounted to a corresponding tier. (The phantom is described, for example in Reference [3].) The phantom was designed such that the orientation of a fiducial marker mounted to a corresponding tier can be estimated by relating the fiducial marker to the locations of the centroids of other fiducial markers. The phantom was scanned in both MR (Spin-Echo, TR=3 sec, TE=14 ms) and CT (kvP=120, exposure=350 mas). The MR image had 256×256×59 voxels. Three CT images were acquired. The first CT image had 512×512×44 voxels. The remaining two CT images had 512×512×45 voxels. Pixel sizes, slice thicknesses, number of fiducial markers and the resulting RMS FAE are shown in Table 2.

TABLE 2

RMS values for Fiducial Angular Error.

| Image Modality | Pixel Size | Slice Thickness | Number of Markers | RMS FAE (degree) |
|---|---|---|---|---|
| The First CT Image | 0.59 mm | 2.5 mm | 23 | 2.8 |
| The Second and Third CT Images | 0.59 mm | 2.0 mm | 16 (8 per image) | 4.8 |
| The MR Image | 0.94 mm | 4.0 mm | 15 | 3.6 |

Registration Accuracy

In one embodiment of the present invention, a simulation was performed to assess the registration method described above in the section of "INCORPORATING MARKER ORIENTATION INTO REGISTRATION". Referring now to FIG. 4, two markers, 410a and 410b, were configured 100 mm apart, each with a varying value of the angle θ between the axis of symmetry 423a (423b) of the marker 410a (410b) and the x-axis 411. The centroids of markers 410a and 410b were located at x=−50 mm and x=50 mm, respectively, on the x-axis 411, which were symmetrical about the y-axis 412. Thus, the configuration is described by Eq. (9) with $N_p=2$ and $N_a=2$. Random, independent, normally distributed perturbations were applied to both centroids and to both axes of symmetry to construct the set of the extended points, $\{p_1, p_2, \hat{a}_1, \hat{a}_2\}$, in the first image. The process was repeated to construct the set of the extended points, $\{q_1, q_2, \hat{b}_1, \hat{b}_2\}$, in the second image. The set of the extended points in the first image and the set of the extended points in the second image were then registered. The resulting rigid-body transformation was applied to the target point 408, $p_T$. The magnitude, $|R p_T + t - p_T|$, of its displacement is called the target registration error (TRE) at the corresponding point. The point perturbations were applied independently to each coordinate of each point. The RMS perturbation distance is called the Fiducial Localization Error (FLE).

Figure 5:
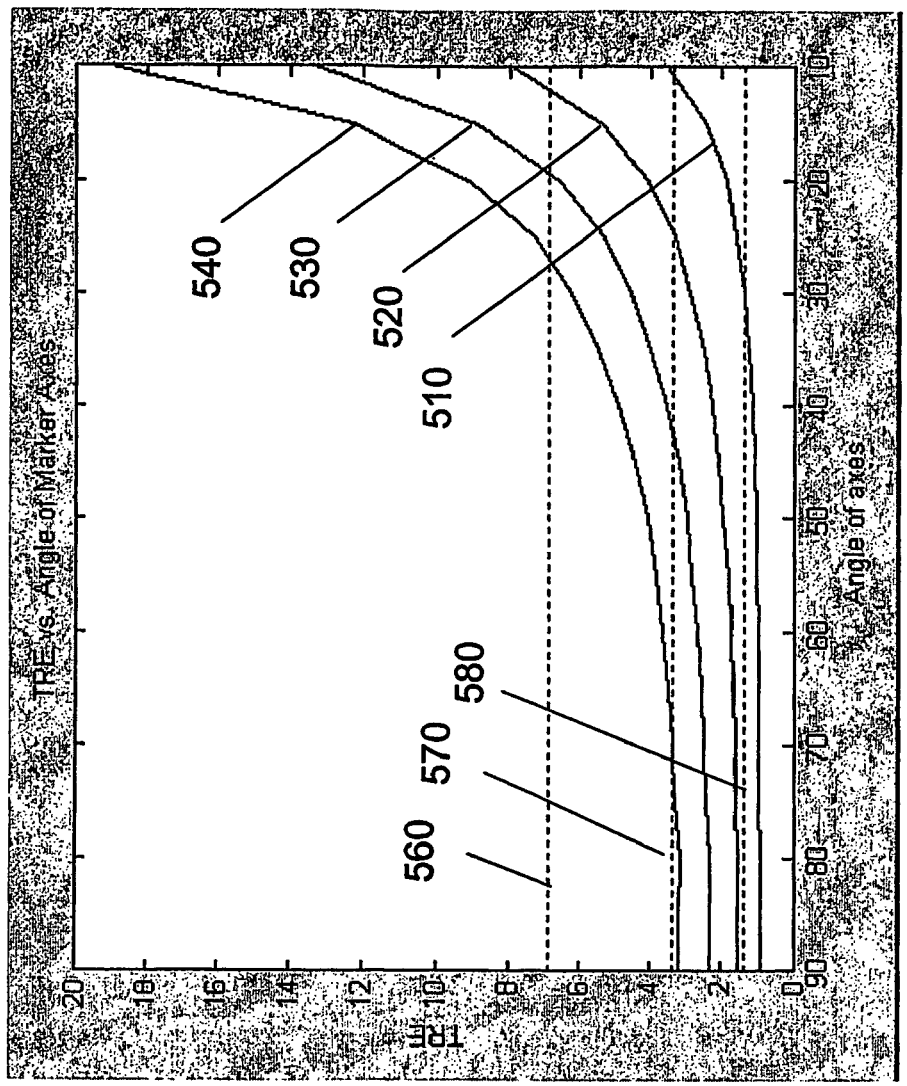
FIG. 5 shows target registration error (TRE) versus θ for the marker configuration of FIG. 4 for different fiducial angular errors (FAE). Curves 510, 520, 530 and 540 are the TRE for degrees 1, 3, 5 and 7 of the FAE, respectively. Dotted lines 560, 570 and 580 are the TRE for the three marker configurations with the third marker being positions 402, 404 and 406, respectively, as shown in FIG. 4.

Experiments were performed (not shown) with varying values of fiducial localization error $FLE_1$ and $FLE_2$, respectively, in the first image and the second image. While the resulting value of TRE was observed, as expected, to depend on the combined $FLE = (FLE_1^2 + FLE_2^2)^{1/2}$ and $FAE = (FAE_1^2 + FAE_2^2)^{1/2}$, it did not depend on the individual values of $FLE_1$ and $FLE_2$. Referring now to FIG. 5, TRE versus θ for the configuration of the fiducial markers shown in FIG. 4 is illustrated, where FLE was set at 1 mm and FAE was varied from 1 to 7 degrees. Curves 510, 520, 530 and 540 are respectively corresponding to the TRE for FAE=1, 3, 5 and 7 degrees. For simplicity, the axis of symmetry 423a of marker 410a and the axis of symmetry 423b of marker 410b were configured in the x-y plane and the angles θ between the axis of symmetry 423a of marker 410a and the x-axis 411 and between the axis of symmetry 423b of marker 410b and the x-axis 411 were set to be identical.

The angle θ was varied from 10 degrees to 90 degrees. A total of 10,000 repetitions were performed for each combination of FAE and θ. The resulting RMS values of TRE are plotted in FIG. 5. For FAE=1, 3, 5, and 7 degrees, the TRE were represented by curves 510, 520, 530 and 540, respectively.

For comparison, TRE was calculated without using marker orientation. Instead, a third marker was located on the y-axis at a varying position. Referring back to FIG. 4, the third marker was marked by the xs with varying positions 402, 404 and 406 on the y-axis 412. The distance of the third marker from positions 402, 404 and 406 to the origin 401 of the x-axis and y-axis were 5 mm, 10 mm and 25 mm, respectively. As the distance of the third marker was reduced from 25 mm to 10 mm to 5 mm from the origin 401 of the two markers 410a and 410b, the value of RMS TRE was calculated [6] and found to increase from 1.4 mm to 3.4 mm to 6.9 mm, which were shown by dot lines 580, 570 and 560, respectively, in FIG. 5. Not surprisingly, as the three markers become more collinear, the quality of the registration is degraded and the use of two markers with marker orientation becomes relatively more beneficial.

Further Discussion

The image registration based on fiducial markers produces highly accurate results simply by measuring the centroids of three or more fiducial markers and bringing them into alignment. When the fiducial markers are nonspherical, additional information about their orientations may be obtained that may serve as an adjunct to the centroid positions. In one embodiment of the present invention, the fiducial markers are cylindrical markers, the axis of symmetry of the marker provides such information. Accurate measurement of the orientation of that axis is made difficult by the typically small size of the marker relative to the voxel sizes and by noise present in the typical MR or CT image. Nevertheless, as shown in Table 2, it is achievable, for at least one type of cylindrical markers, to estimate the direction of the axis to within about 3 to 5 degrees (RMS values of FAE) in these modalities.

Employing the additional orientation information for the purpose of rigid-body image registration requires an extension of the standard methods, which employ only centroid information. It is shown that the simple extension results in a closed-form solution. One clear advantage of the technique is that it is capable of producing an image registration with only two markers, as opposed to a minimum of three markers required in the standard registration methods. The examples, shown in FIG. 5, indicate that for a combined FLE of 1 mm and a combined FAE ranging from 1 to 7 degrees, the marker configuration shown in FIG. 4 yields TRE values ranging from 0.9 mm to 3.4 mm for reasonable values of $\theta$. The consistent improvement as $\theta$ is increased toward 90 degrees is predictable. The orientations of the marker axes provide information about the relative rotation of the two spaces about all axes except themselves, and the more perpendicular the axes are to the marker axes, the more accurate the information is. The combination of the two marker centroids, on the other hand, provides rotational information about all axes except the x-axis, and that information is more accurate for axes that are more perpendicular to the x-axis. Thus, as the marker axes become more perpendicular to the x-axis, their contributions to orientation information become more complementary to the information provided by the two centroids. It is therefore clear that $\theta$ should be as close as possible to 90 degrees, but the results of examples show that degradation is minor down to about 70 degrees.

Calculation of the combined RMS FAE, FAE=$(FAE_1^2+FA_2^2)^{1/2}$, from all combinations of the values given in Table 2 produces values ranging from 4.0 to 6.8 degrees. Thus, the RMS FAE values employed in FIG. 5 bracket the values of the combined FAE involving these markers and these modalities (i.e., CT-CT, CT-MR, and MR-MR). These values of TRE are comparable to that achievable with three markers when the markers are configured such that the target is outside the triangle formed by the markers, as shown in FIG. 4 and becomes more important as the marker configuration becomes more collinear. This situation may be important for certain applications when orientation information is available and there are restrictions on the placement of the markers relative to the targets of interest; it is clearly important when only two markers are available and when the markers are nearly collinear.

The results of these examples show that according to the present invention, it is possible to determine the orientations of the axis of symmetry of cylindrical markers in CT and MR images to within about 3 to 5 degrees and to utilize those orientations in a closed-form registration algorithm to achieve a target registration errors of about 2 to 3 millimeters for a configuration in which two markers are separated by 100 mm with a target 50 mm from their mean position. Further work is needed to explore the effects of variations of marker numbers, configurations, axes orientation, and altering marker shape. A larger ratio of the height to diameter of a fiducial marker, for example, might be expected to reduce FAE. While the use of marker orientation unlikely ever to be as effective as the use of additional, widely-spaced markers, the results may be important for situations in which only two markers are available or only nearly collinear configurations are feasible.

While there has been shown various embodiments of the present invention, it is to be understood that certain changes can be made in the form and arrangement of the elements of the apparatus and steps of the methods to practice the present invention as would be known to one skilled in the art without departing from the underlying scope of the invention as is particularly set forth in the Claims. For examples, while examples set forth above are related to practice the present invention for cylindrical markers, the present invention can be practiced for other shapes of fiducial markers as well. Furthermore, the embodiments described above are only intended to illustrate the principles of the present invention and are not intended to limit the claims to the disclosed elements.

REFERENCE LIST

[1] J. M. Fitzpatrick, D. L. G. Hill, and C. R. Maurer, Jr., Registration, *Medical Inage Processing*, Volume II of the Handbook of Medical Imaging, M. Sonka and J. M. Fitzpatrick, ed., SPIE Press (July, 2000).

[2] C. H. Yan, R. T. Whalen, G. S. Beaupre, T. S. Sumanaweera, S. Y. Yen, S. Napel, A new frame-based registration algorithm, *Medical Physics* 25 (1): 121-128 (January 1998).

[3] C. R. Maurer, Jr., J. M. Fitzpatrick, M. Y. Wang, R. L. Galloway, Jr., R. J. Maciunas, G. S. Allen, Registration of head volume images using implantable fiducial markers, *IEEE Transactions on Medical Imaging* 16, 447-462 (August 1997).

[4] M. Y. Wang, C. R. Maurer, Jr., J. M. Fitzpatrick, and R. J. Maciunas, An automatic technique for finding and localizing externally attached markers in CT and MR volume images of the head, *IEEE Transactions on Biomedical Engineering* 43, 627-637 (June 1996).

[5] M. Y. Wang, *Fiducial Marker Recognition and Localization for Image-Guided surgery Using Point-Based Registration*, Ph.D. Dissertation, Computer Science, Vanderbilt University, Nashville, Tenn. (May 1998).

[6] J. M. Fitzpatrick, J. B. West, C. R. Maruer, Jr., Predicting error in rigid-body, point-based image registration, *IEEE Transactions on Medical Imaging* 17, 694-702 (October 1998).

What is claimed is:

1. A method for determining an orientation of a base to which a fiducial marker is detachably mounted, wherein the base has an axis of symmetry, $a_b$, representing the orientation, a threaded portion at a first end threaded into a portion of a human anatomy at a predetermined location, and an engagement portion at a second end opposing the first end, and wherein the fiducial marker has an axis of symmetry, $a_m$, and is detachably mounted to the engagement portion of the second end of the base, comprising of the steps of:

determining the axis of symmetry for the fiducial marker; and choosing the determined axis of symmetry of the fiducial marker as the axis of symmetry of the base, wherein the determining step comprises the steps of:

a. acquiring an image having the fiducial marker from the portion of the human anatomy;

b. segmenting the fiducial marker into a plurality of voxels from the acquired image;

c. estimating the centroid of the fiducial marker from the segmented fiducial marker image;

d. estimating the axis of symmetry of the fiducial marker at the estimated centroid;

e. simulating an image of the fiducial marker at the estimated centroid and the estimated axis of symmetry;

f. registering the simulated image of the fiducial marker with the acquired image of the fiducial marker so as to obtain a registered centroid and a registered axis of symmetry of the fiducial marker in the acquired image;

g. updating the estimated centroid and the estimated axis of symmetry of the fiducial marker to the registered centroid and the registered axis of symmetry of the fiducial marker, respectively;

h. repeating steps (e)-(g) until both differences between the estimated centroid and the registered centroid and differences between the estimated axis of symmetry and the registered axis of symmetry are substantially small; and i. choosing the last registered axis of symmetry as the axis of symmetry of the fiducial marker.

2. The method of claim 1, wherein the step of estimating the centroid of the fiducial marker is performed with an intensity weighting method.

3. The method of claim 1, wherein the step of estimating the axis of symmetry of the fiducial marker comprises the steps of:

a. decomposing principal axes of the fiducial marker at the estimated centroid of the fiducial marker;

b. calculating moments of inertia for the decomposed principal axes; and c. identifying the axis of the symmetry from the calculated moment of inertia.

4. The method of claim 3, wherein the moment of inertia of the axis of the symmetry is equal to $d^2/8$ for a cylindrical fiducial marker, d being the diameter of the cylindrical fiducial marker.

5. The method of claim 1, wherein the simulating step comprises the steps of:

a. setting intensity of a voxel that is completely inside the fiducial marker to the maximum intensity values, $I_{max}$, of the voxel values in the acquired image;

b. setting intensity of a voxel that is completely outside the fiducial marker to zero; and c. defining intensity of a voxel that crosses the edge of the fiducial marker as a form of $$I = \frac{V_{in}}{V} I_{max},$$

wherein $V_{in}$ is the volume of the voxel that lies inside the fiducial marker, V is the volume of the entire voxel, and $I_{max}$ is the voxel intensity of the voxel completely inside the fiducial marker.

6. The method of claim 5, wherein the defining step comprises the steps of:

a. dividing the voxel that crosses the edge of the fiducial marker into m×n×p subvoxels, wherein each of m, n, p is an integer;

b. designating a subvoxel as being inside the fiducial marker if its centroid is inside the fiducial marker and as being outside the fiducial marker if its centroid is outside the fiducial marker;

c. accumulating the number of the subvoxels whose centroids are inside the fiducial marker; and d. determining $V_{in}/V$ by dividing the accumulated number by the total number, m×n×p, of the subvoxels of the voxel so as to obtain the intensity of the voxel that crosses the edge of the fiducial marker, I.

7. The method of claim 1, wherein the registering step is performed with an optical flow registration.

8. The method of claim 1, wherein the acquired image comprises a tomographic image.

9. The method of claim 8, wherein the tomographic image comprises a computed tomographic (CT) image.

10. The method of claim 8, wherein the tomographic image comprises a magnetic resonance (MR) image.

11. A system of image guidance through a portion of a human anatomy, comprising:

a. a number, M, of bases, each base having an axis of symmetry, $a_b$, representing the orientation of the base, a threaded portion at a first end threaded into the portion of a human anatomy at a predetermined location and an engagement portion at a second end opposing the first end;

b. a number M of fiducial markers, each fiducial marker having an axis of symmetry, $a_m$, and being detachably mounted to a corresponding base at the engagement portion of the second end of the base; and c. a platform having a number M of bosses, each boss being mounted to the engagement portion of a corresponding base such that the boss lines up with the base.

12. The system of claim 11, further comprising means for acquiring a three-dimensional tomographic image from the portion of the human anatomy containing the number M of fiducial markers for identifying the centroid and the axis of symmetry of each fiducial marker as so to determine the position and orientation of its corresponding base.

13. The system of claim 12, further comprising means for identifying the centroid and axis of symmetry of a fiducial marker from the acquired image of the fiducial marker.

14. The system of claim 11, wherein the portion of the human anatomy is a human head.

15. The system of claim 11, wherein $a_b$ is substantially identical to $a_m$ when the fiducial marker is mounted to the corresponding base.

16. The system of claim 11, wherein each of the bases is a solid cylinder.

17. The system of claim 11, wherein each of the fiducial markers has a cylindrical cavity.

18. The system of claim 17, wherein the cylindrical cavity is filled with an imagable material.

19. The system of claim 18, wherein the imagable material comprises a fluid that is visible in a computed tomographic (CT) image.

20. The system of claim 18, wherein the imagable material comprises a fluid that is visible in a magnetic resonance (MR) image.

21. The system of claim 12, wherein the three-dimensional tomographic image comprises a computed tomographic (CT) image.

22. The system of claim 12, wherein the three-dimensional tomographic image comprises a magnetic resonance (MR) image.

23. The system of claim 11, wherein M is an integer greater than one.

24. A method for registering a first image with a second image, wherein the first image has at least two fiducial markers each having an axis of symmetry, and the second image has at least two fiducial markers each having an axis of symmetry and corresponding to a fiducial marker in the first image, the at least two fiducial markers of the first image and the at least two fiducial markers of the second image being orientated such that the axis of symmetry of at least one of the at least two fiducial markers for each of the first image and the second image is nonparallel to a line on which the at least two fiducial markers lie in the corresponding image, comprising the steps of:
   a. finding the centroid of each of the at least two fiducial markers in the first image;
   b. finding the axis of the symmetry of each of the at least two fiducial markers in the first image;
   c. constructing a set of points for the at least two fiducial markers in the first image, the set of points including a vector of the centroid and an unit vectors of the axis of the symmetry of each of the at least two fiducial markers in the first image;
   d. repeating steps (a)-(c) in the second image for the at least two fiducial markers in the second image so as to construct a set of points for the at least two fiducial markers in the second image corresponding to the set of points in the first image; and
   e. determining a transformation matrix from the set of points in the first image and the set of points in the second image so as to register the first image with the second image.

25. The method of claim 24, wherein each of the fiducial markers is a cylinder.

26. The method of claim 25, wherein the axis of symmetry of each fiducial marker is an axis having a cylindrical symmetry.

27. The method of claim 24, wherein the transformation matrix corresponds to a rigid-body transformation.

28. The method of claim 27, wherein the transformation matrix is calculated with a closed-form algorithm.

29. The method of claim 28, wherein the closed-form algorithm comprises a singular value decomposition (SVD) method.

30. A system for registering a first image with a second image, wherein the first image has at least two fiducial markers each having an axis of symmetry, and the second image has at least two fiducial markers each having an axis of symmetry and corresponding to a fiducial marker in the first image, the at least two fiducial markers of the first image and the at least two fiducial markers of the second image being orientated such that the axis of symmetry of at least one of the at least two fiducial markers for each of the first image and the second image is nonparallel to a line on which the at least two fiducial markers lie in the corresponding image, comprising a central processing unit (CPU) programmed for performing the steps of:
   a. finding the centroid of each of the at least two fiducial markers in the first image;
   b. finding the axis of the symmetry of each of the at least two fiducial markers in the first image;
   c. constructing a set of points for the at least two fiducial markers in the first image, the set of points including a vector of the centroid and an unit vectors of the axis of the symmetry of each of the at least two fiducial markers in the first image;
   d. repeating steps (a)-(c) in the second image for the at least two fiducial markers in the second image so as to construct a set of points for the at least two fiducial markers in the second image corresponding to the set of points in the first image; and
   e. determining a transformation matrix from the set of points in the first image and the set of points in the second image so as to register the first image with the second image.

31. The system of claim 30, wherein the fiducial marker is a cylinder.

32. The system of claim 31, wherein the axis of symmetry of each fiducial marker is an axis having a cylindrical symmetry.

33. The system of claim 30, wherein the transformation matrix corresponds to a rigid-body transformation.

34. The system of claim 33, wherein the transformation matrix is calculated with a closed-form algorithm.

35. The system of claim 34, wherein the closed-form algorithm comprises a singular value decomposition (SVD) method.

36. The system of claim 30, wherein the central processing unit is associated with a computer.

* * * * *